United States Patent
Terwey (10) Patent No.: US 8,298,259 B2
(45) Date of Patent: Oct. 30, 2012

(54) TISSUE PUNCTURE CLOSURE DEVICE WITH ACTUATABLE AUTOMATIC SPOOL DRIVEN COMPACTION SYSTEM

(75) Inventor: Russell D. Terwey, St. Michael, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 352 days.

(21) Appl. No.: 12/773,547

(22) Filed: May 4, 2010

(65) Prior Publication Data

US 2010/0286727 A1 Nov. 11, 2010

Related U.S. Application Data

(60) Provisional application No. 61/175,737, filed on May 5, 2009.

(51) Int. Cl.
*A61B 17/08* (2006.01)
*A61B 17/04* (2006.01)
(52) U.S. Cl. ........................ 606/213; 606/232
(58) Field of Classification Search .................. 606/213, 606/232
See application file for complete search history.

(56) References Cited

U.S. PATENT DOCUMENTS

| | | | |
|---|---|---|---|
| 6,045,569 | A | 4/2000 | Kensey et al. |
| 6,090,130 | A | 7/2000 | Nash et al. |
| 6,179,963 | B1 | 1/2001 | Begemann et al. |
| 7,250,057 | B2 | 7/2007 | Forsberg |
| 7,618,436 | B2 | 11/2009 | Forsberg |
| 7,749,247 | B2 | 7/2010 | Tegg |
| 7,749,248 | B2 | 7/2010 | White et al. |
| 2005/0085851 | A1* | 4/2005 | Fiehler et al. .............. 606/213 |
| 2007/0255314 | A1 | 11/2007 | Forsberg |
| 2010/0234883 | A1 | 9/2010 | White et al. |

FOREIGN PATENT DOCUMENTS

WO 2006124245 A2 11/2006

\* cited by examiner

*Primary Examiner* — Darwin Erezo
*Assistant Examiner* — Shaun L David
(74) *Attorney, Agent, or Firm* — Holland & Hart (57) ABSTRACT

A tissue puncture closure device includes an anchor, a sealing plug, a suture coupled to the sealing plug, a compaction arrangement, and an automatic driving assembly. The automatic driving assembly includes first and second spool members and an actuation member. The first spool member is configured to coil a portion of the suture. The second spool member is configured to coil a portion of the compaction arrangement. The actuation member is coupled to the first and second spool members. Activation of the actuation member releases the first spool member for rotation to apply a tension force in the suture, and releases the second spool member for rotation to distally advance a portion of the compaction arrangement to compress the sealing plug.

20 Claims, 8 Drawing Sheets

TISSUE PUNCTURE CLOSURE DEVICE WITH ACTUATABLE AUTOMATIC SPOOL DRIVEN COMPACTION SYSTEM

RELATED APPLICATION

This application claims the benefit of U.S. Provisional Application No. 61/175,737, filed 5 May 2009, which is hereby incorporated by reference herein in its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing plug at the tissue puncture site. Successful deployment of the sealing plug, however, typically involves manually ejecting it from within a device sheath. The sealing plug may also be compacted down to an outer surface of the tissue puncture using, for example, a compaction member such as a compaction tube. The compaction procedure may commence until the device sheath (within which the compaction tube is located) has been removed so as to expose the compaction tube for manual grasping. Under certain conditions, removal of the sheath prior to compacting the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

One aspect of the present disclosure relates to a tissue puncture closure device that includes an anchor, a sealing plug, a suture coupled to the sealing plug, a compaction arrangement, and an automatic driving assembly. The automatic driving assembly includes first and second spool members and an actuation member. The first spool member is configured to coil a portion of the suture. The second spool member is configured to coil a portion of the compaction arrangement. The actuation member is coupled to the first and second spool members. Activation of the actuation member releases the first spool member for rotation, thereby applying a tension force in the suture, and releases the second spool member for rotation to distally advance a portion of the compaction arrangement to compress or distally advance the sealing plug.

The tissue puncture closure device may also include a housing sized to retain the automatic driving assembly, and the automatic driving assembly is movable within the housing. The tissue puncture closure device may also include an insertion sheath connected to the housing. The compaction arrangement may include a tube portion arranged to compress the sealing plug, and a coil portion at least partially wrapped about the second spool member. The tissue puncture closure device may further include a housing sized to retain the automatic driving assembly, and the actuation member includes an actuation member accessible from outside of the housing. The first and second spool members may be operable independent of each other. The actuation member may be configured to concurrently release the first and second spool members. The actuation member may be configured to restrict rotation of the first and second spool members in one direction, and the spool members may be free to rotate in an opposite direction prior to and after activation of the actuation member.

Another aspect of the present disclosure relates to a tissue puncture closure device that is adapted for partial insertion into and sealing of a tissue puncture in an internal tissue wall that is accessible through a percutaneous incision. The device includes an anchor, a sealing plug, a suture, and a compaction arrangement. The anchor is disposed on a distal side of the internal tissue wall. The sealing plug is disposed on a proximal side of the internal tissue wall. The suture is coupled at a distal end portion to the anchor and the sealing plug and is slidably disposed on the suture proximal of the anchor. The compaction arrangement includes a compaction tube, first and second spool members, and an actuation member. The compaction tube is disposed on the suture and configured to drive the sealing plug along the suture distally towards the anchor. The first spool member is configured to have a proximal end portion of the suture wound there about. The second spool member is configured to have a portion of the compaction arrangement wound there about. The actuation member is disengageably coupled to the first and second spool members, wherein activation of the actuation member releases the first spool member to rotate to provide a tension force in the suture, and releases the second spool member to rotate thereby advancing the compaction member distally to compress or advance the sealing plug.

The tissue puncture closure device may also include a housing, and the first and second spool members are slidable within the housing in a distal direction. The first and second spool members may rotate in opposite directions when released by the actuation member. The first and second spool members may be operable independent of each other. The first and second spool members may be arranged non-coaxially relative to each other. The tissue puncture closure device may further include a carrier tube, and the sealing plug and the compaction tube are positioned in the carrier tube. The carrier tube may be operatively coupled to at least one of the first and second spool members, wherein sliding of the first and second spool members within the housing moves the carrier tube relative to the housing.

A further aspect of the present disclosure relates to a method of sealing a tissue puncture in an internal tissue wall that is accessible through a percutaneous incision. The method may include providing a tissue puncture closure device having an anchor, a sealing plug, a suture coupled to the anchor and sealing plug, a compaction arrangement, first and second spool members, and an actuation member. A portion of the suture may be wound about the first spool member, and at least a portion of the compaction arrangement may be wound about the second spool member. The method may also include inserting the tissue puncture closure device into the percutaneous incision, deploying the anchor into the tissue puncture, at least partially withdrawing the closure device from the percutaneous incision, and actuating the actuation member to release the first and second spool members. Releasing the first and second spool members permits rotation of the first spool member thereby creating a tension force in the suture and permitting rotation of the second spool member to compress or advance the sealing plug toward the anchor with the compaction arrangement.

The tissue puncture closure device may further include a housing sized to retain at least the first and second spool members, wherein actuating the actuation member includes engaging a portion of the actuation member that is exposed outside of the housing. The method may also include providing an insertion sheath, and inserting the insertion sheath into the percutaneous incision may include inserting a portion of the tissue puncture closure device into the insertion sheath. Deploying the anchor may include advancing the anchor distally beyond a distal end of the insertion sheath. The method may also include at least partially withdrawing the insertion sheath from the percutaneous incision prior to at least partially withdrawing the closure device. The tissue puncture closure device may further include a carrier tube. The sealing plug may be positioned in the carrier tube, and withdrawing the tissue puncture closure device may include at least partially withdrawing the carrier tube and compaction arrangement from the percutaneous incision while leaving the sealing plug positioned in the percutaneous incision. Withdrawing the tissue puncture closure device may include unwinding a portion of the suture from the first spool member, and actuating the actuation member releases the first spool member to wind up a portion of the suture.

Additional advantages and novel features will be set forth in the description which follows or may be learned by those skilled in the art through reading these materials or practicing the examples disclosed herein. The advantages of the invention may be achieved through the means recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the invention.

Throughout the drawings, identical reference numbers designate similar, but not necessarily identical, elements.

Throughout the drawings, identical reference numbers designate similar, but not necessarily identical, elements.

DETAILED DESCRIPTION

As mentioned above, vascular procedures are conducted throughout the world and require access to a vessel through a puncture. Most often, the vessel is a femoral artery. To close the puncture following completion of the procedure, many times a closure device is used to sandwich the puncture between an anchor and a sealing plug. However, sometimes the sealing plug is difficult to eject from the closure device and may not properly seat against an exterior situs of the arteriotomy. If the plug does not seat properly against the arteriotomy, there is a potential for prolonged bleeding. The present disclosure describes methods and apparatus that facilitate sealing plug ejection and proper placement of the sealing plug.

While the vascular instruments shown and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the term "compact," "compacting," or "compaction" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The term "effecting" means producing an outcome, achieving a result, or bringing about. The words "including" and "having," as used in the specification, including the claims, have the same meaning as the word "comprising."

Referring now to the drawings, and in particular to FIGS. 1-4, an example tissue puncture closure device 100 (also referred to as a closure device or a puncture closure device) is shown. The tissue puncture closure device includes a carrier tube 102 with a filament or suture 104 extending at least partially there through. The closure device 100 also includes a first or proximal end 106 and a second or distal end 107. External to a second or distal end 107 of the carrier tube 102 is an anchor 108. The anchor may be an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented, bound together fibrous material. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction tube 112 (also referred to herein as a compaction member) disposed therein. The compaction tube 112 is slidingly mounted on the suture 104 and may be used by an operator to compact or compress the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 1:
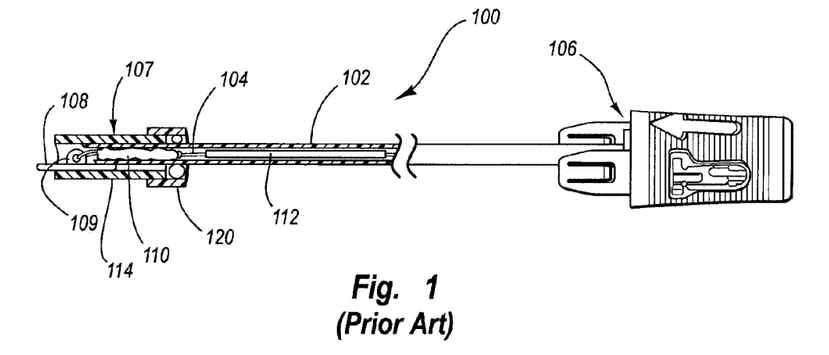
FIG. 1 is a partial cut-away view of a tissue puncture closure device according to the prior art.
Figure 2:
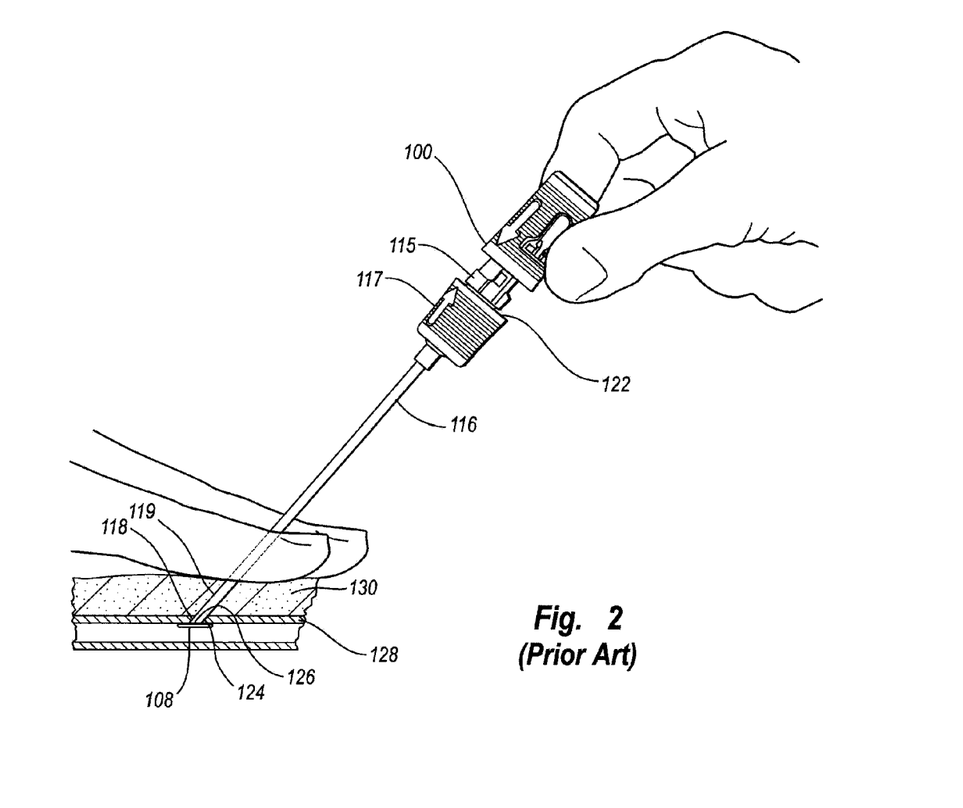
FIG. 2 is a side view of the tissue puncture closure device of FIG. 1 engaged with an artery according to the prior art.
Figure 3:
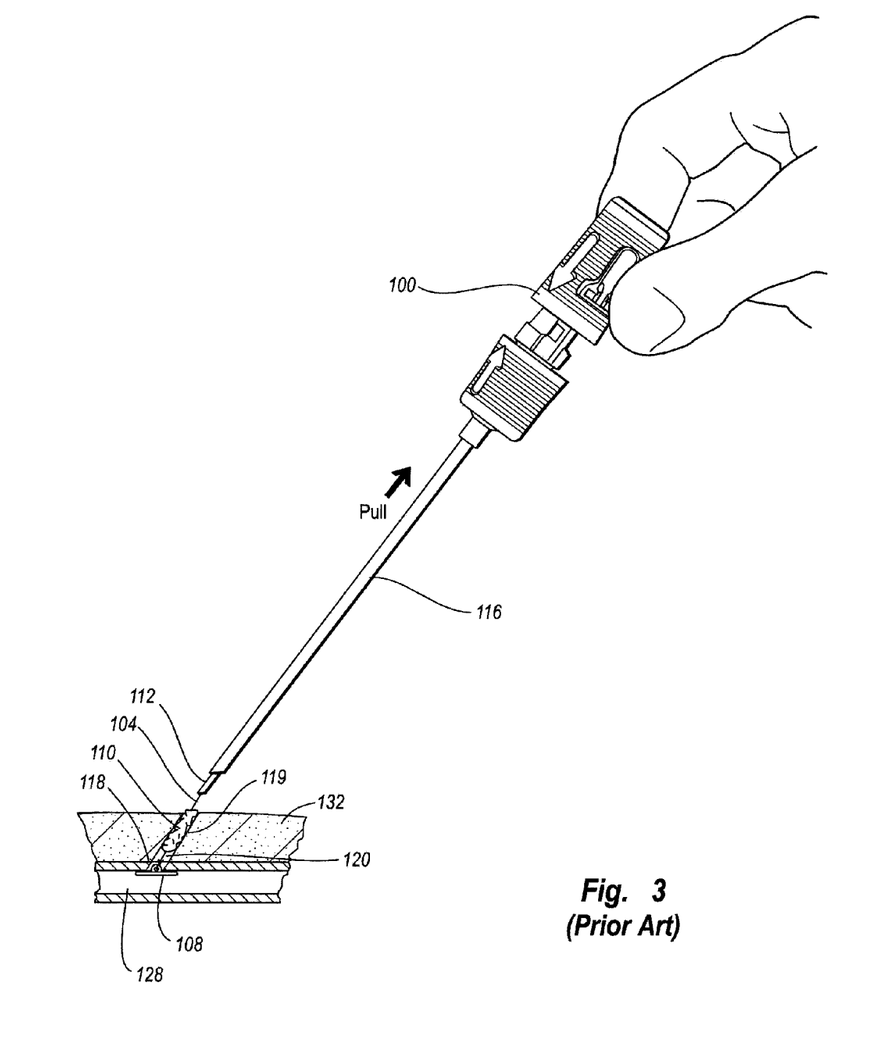
FIG. 3 is a side view of the tissue puncture closure device of FIG. 1 being withdrawn from an artery to deploy a collagen sponge according to the prior art.
Figure 4:
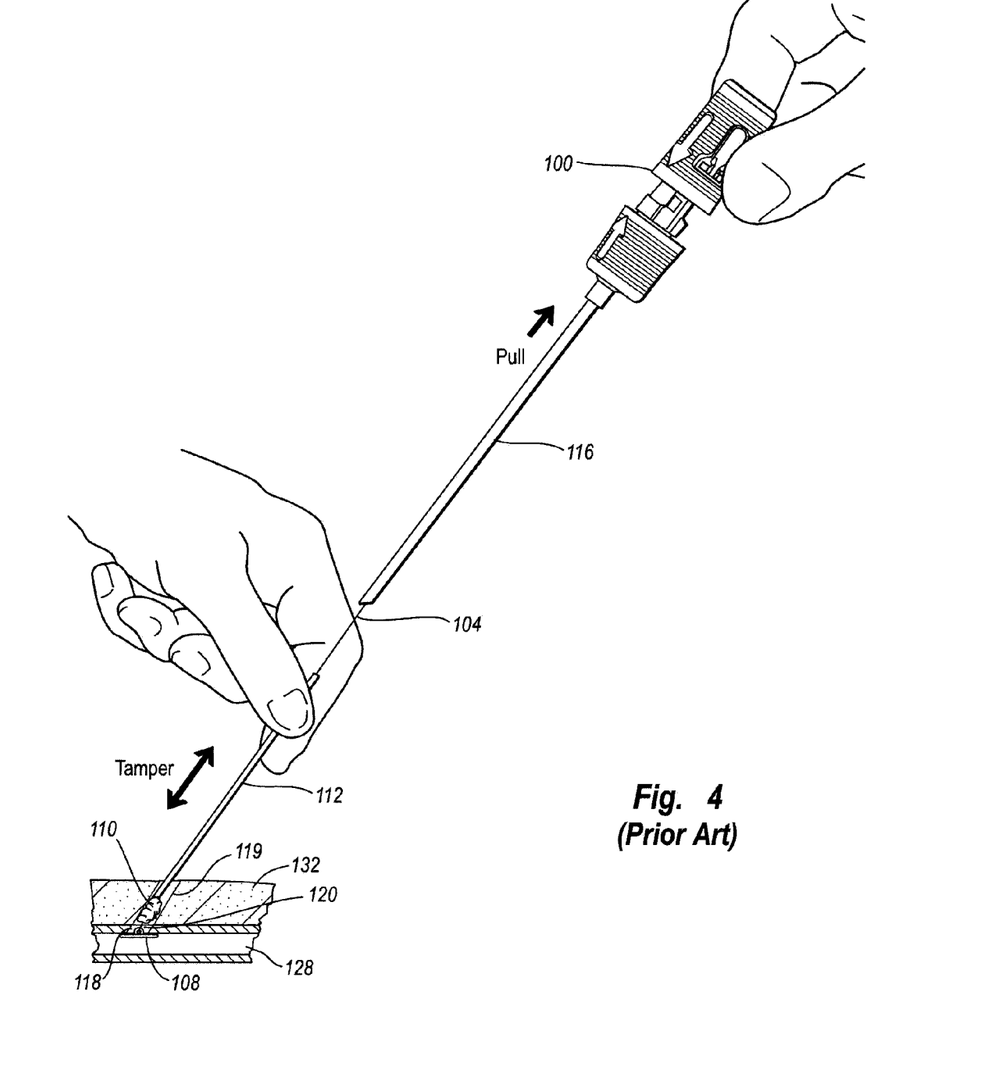
FIG. 4 is a side view of the tissue puncture closure device of FIG. 1 illustrating compaction of the collagen sponge according to the prior art.

The flush arrangement of the anchor 108 and carrier tube 102 allows the anchor 108 to be inserted into a procedural sheath such as insertion sheath 116 as shown in FIGS. 2-4, and eventually through an arterial puncture 118. The insertion sheath 116 is shown in FIGS. 2-4 inserted through a percutaneous incision tract 119 and into an artery 128. The bypass tube 114 may include an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 and the bypass tube 114, releasing the anchor 108 from the bypass tube 114 (see FIG. 1). The anchor 108 remains in the flush arrangement shown in FIG. 1 following release from the bypass tube 114, limited in movement by the insertion sheath 116. The puncture closure device 100 is advanced distally until a pair of biased finger locking members 115 of the puncture closure device 100 lockingly engage with a hub member 117 of the insertion sheath (see FIG. 2).

The insertion sheath 116 may include a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. After the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the closure device 100 and the insertion sheath 116 are withdrawn together, ejecting the collagen pad 110 from the carrier tube 102 into the incision tract 119 and exposing the compaction tube 112. With the compaction tube 112 fully exposed as shown in FIG. 4, the collagen pad 110 is manually compacted, and the anchor 108 and collagen pad 110 are cinched together and held in place with the self-tightening slip-knot on the suture 102. The tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and remain in place while the tissue puncture 118 heals.

Using the typical tissue puncture closure device 100 described above, however, it may be difficult to eject and compact of the collagen pad 110. The insertion sheath 116 resists deformation as the collagen pad 110 is ejected from the carrier tube and compaction may not commence until the insertion sheath 116 has been removed so as to expose the compaction tube 112 for manual grasping. Under certain conditions, removal of the insertion sheath 116 prior to compacting the collagen pad 110 causes the collagen pad 110 to retract or displace proximally from the tissue puncture 118, creating an undesirable gap between the collagen pad 110 and the tissue puncture 118. The gap may remain even after compaction, and sometimes results in only a partial seal and bleeding from the tissue puncture 118.

Therefore, the present specification describes a medical device such as a tissue puncture closure device that is capable of retracting a procedural sheath relative to a closure device, exposing a distal end of the closure device prior to ejecting a sealing plug. The closure device also at least partially automatically drives the sealing plug toward a tissue puncture upon withdrawal of the tissue puncture closure device from the tissue puncture site. The mechanism for automatically driving the sealing plug may be selectably disengagable.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-I, a medical device, for example a tissue puncture closure device 200, is shown according to one embodiment of the present disclosure. The closure device 200 is shown assembled with a procedural sheath 216 in FIG. 5A. FIGS. 5B-I illustrate the closure device 200 assembled and inserted through the procedural sheath 216 and into a lumen 232 of a vessel or artery 228. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the embodiments below are directed to the sealing off of percutaneous punctures in arteries, such devices have much more wide-spread applications and may be used for sealing punctures or incisions in other types of tissue walls as well. Thus, the sealing of a percutaneous puncture in an artery, shown herein, is merely illustrative of one particular use of the closure device 200 of the present disclosure.

The closure device 200 includes a first or proximal end portion 206 and a second or distal end portion 207. A carrier tube 202 extends from the proximal end portion 206 to the distal end portion 207 and includes an outlet 213 (see FIG. 5C) at the distal end portion 207. The distal end portion 207 may include a slit that facilitates easier removal of components of the closure device 200 from the carrier tube 202.

The carrier tube 202 may be made of plastic or other material and is designed for insertion through the procedural sheath 216. The procedural sheath 216 is designed for insertion through a percutaneous incision 219 in a tissue layer 230 and into the lumen 232. The lumen 232 defines an interior portion of a vessel such as a femoral artery 228. The artery 228 includes an artery wall 234.

At the distal end portion 207 of the carrier tube 202 there is an anchor 208 and a sealing plug 210. The anchor 208 of the present embodiment is typically an elongated, stiff, low-profile member arranged to be seated inside the artery 228 against the artery wall 234 contiguous with a tissue puncture 218. The anchor 208 is preferably made of a biologically resorbable polymer. The anchor 208 may include an eye 209 for connection to the suture 204. The sealing plug 210 is formed of, for example, a compressible sponge, foam, or fibrous mat made of a non-hemostatic biologically resorbable material such as collagen. The sealing plug 210 may be configured in any shape so as to facilitate sealing the tissue puncture 218.

Figure 5A:
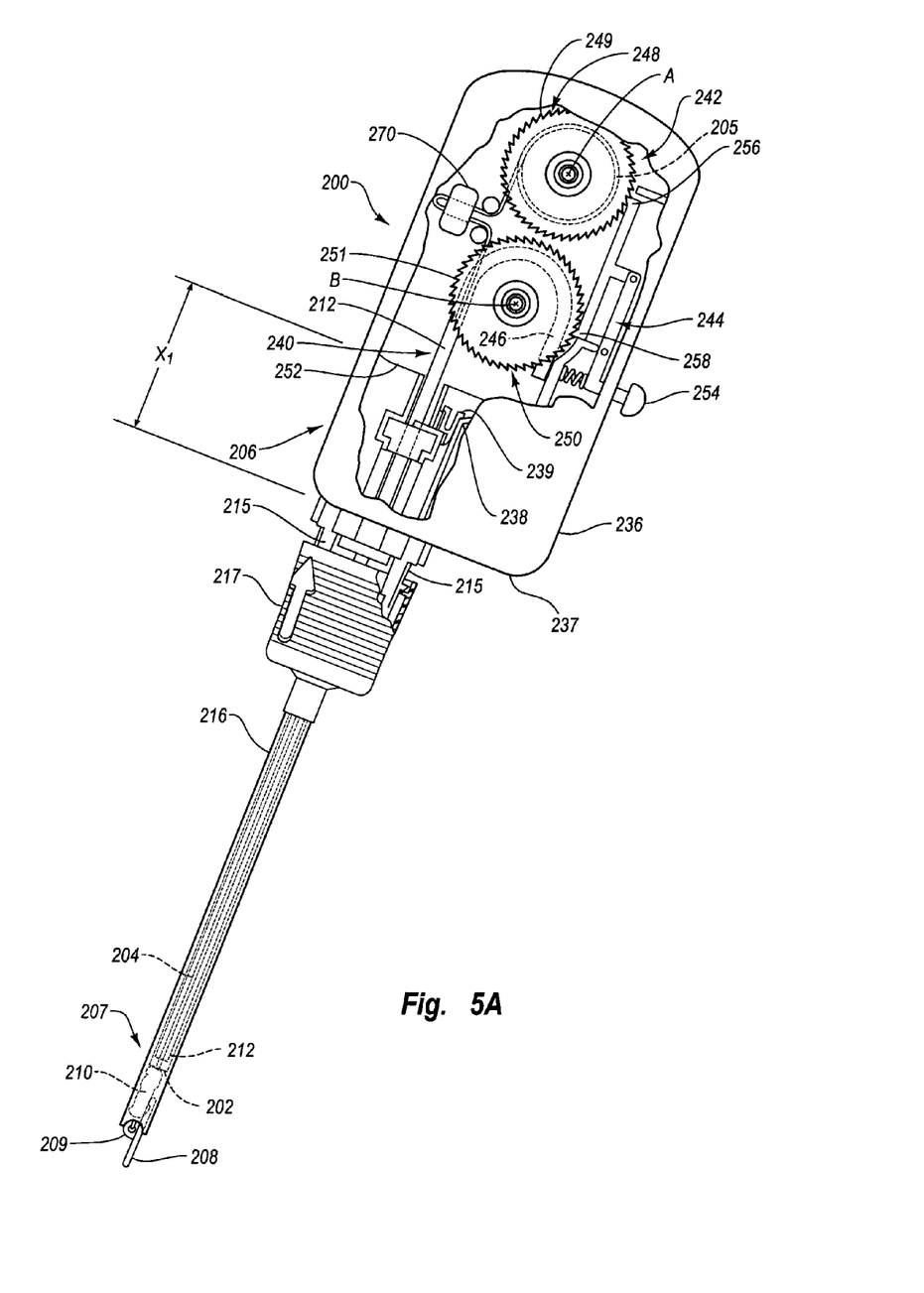
FIG. 5A is a perspective assembly view of a tissue puncture closure device with an automatic compaction or driving mechanism according to one embodiment of the present disclosure.

The sealing plug 210 and anchor 208 are connected to one another by a filament or suture 204. The suture 204 usually comprises a biologically resorbable material. The anchor 208, the sealing plug 210, and the suture 204 may be collectively referred to as the "closure elements" below. As shown in FIG. 5A, the anchor 208 is initially arranged adjacent to and exterior of the distal end portion 207 of the carrier tube 202, while the sealing plug 210 is initially disposed within the carrier tube 202. The anchor 208 is shown nested in its low profile configuration along the carrier tube 202 to facilitate insertion into the lumen 232 and deployed with a first surface 236 abutting the artery wall 234 in FIGS. 5B-C.

The suture 204 extends distally from the first end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock the anchor and plug together, sealing the tissue puncture 218.

The carrier tube 202 houses a compaction device, such as a compaction tube 212, for advancing the sealing plug 210 along the suture 204 toward the anchor 208. The compaction tube 212 may be movable axially relative to the carrier tube 202. The compaction tube 212 may be part of a compaction arrangement 240 that includes a coiled portion 246 (see FIG. 5A) and the compaction tube 212. The compaction arrangement 240 may be configured as a single unitary piece. Alternatively, the compaction arrangement 240 may include multiple pieces or segments that are operatively coupled together.

The compaction tube 212 is shown located partially within the carrier tube 202 and proximal of the sealing plug 210. A portion of the compaction tube 212 may also extend into a handle or housing 236 of the closure device 200. The compaction tube 212 is preferably an elongated tubular or semi-tubular rack that may be rigid or flexible and formed of any suitable material. For example, according to one embodiment, the compaction tube 212 is made of polyurethane. The suture 204 may extend through at least a portion of the compaction tube 212. For example, as shown in FIG. 5A, the suture 204 extends along the compaction tube 212 between the first and second end portions 206, 207. However, the suture 204 is not directly connected to the compaction tube 212. Accordingly, the suture 204 and the compaction tube 212 may slide past one another.

According to the embodiment of FIGS. 5A-I, the suture 204 attaches to a portion of an automatic driving assembly 242. The automatic driving assembly 242 includes a first spool member 248, a second spool member 250, and a support or slide member 252. The carrier tube 202 may be operatively coupled to the support member 252. The first and second spool members 248, 250 may be spring loaded, wherein rotating the first and second spool members 248, 250 in a first direction "cocks" the spring of the spools and release of the cocked first and second spool members 248, 250 results in automatic rotation in an opposite direction.

The first spool member 248 is arranged in the handle 236 and carried by the support member 252. The first spool member 248 is configured to retain a coiled portion 205 of the suture 204. The first spool member 248 may include a plurality of spool teeth 249 or other contact features arranged around a periphery surface thereof that are configured for contact by features of an actuation member 244.

The second spool member 250 is also arranged in the handle 236 and carried by the support member 252. The second spool member 250 may be configured to retain a coiled portion of a compaction arrangement 240, namely the coiled portion 246 of the compaction arrangement 240. The second spool member 250 may include a plurality of spool teeth 251 or other contact structure arranged around a periphery surface thereof that are configured for contact by the actuation member 244. Further discussion concerning the operation of the automatic driving assembly 242 is provided below, in particular with reference to FIGS. 5D-I.

The suture 204 and the coiled portion 246 of the compaction arrangement 240 are shown in FIG. 5A wrapped about the first and second spool members 248, 250, respectively, in the same clockwise (CW) direction. In other arrangements, the suture 204 and the coiled portion 246 may be wrapped about the first and second spool members 248, 250, respectively, in opposite directions. A portion of the suture 204 may pass through a tensioning member 270. The tensioning member 270 may be configured to maintain tension in the suture 204 during winding or unwinding of the suture 204 on the first spool member 248. The tensioning member 270 may be carried by the support member 252.

The first and second spool members 248, 250 may both be carried by the support member 252 of the automatic driving assembly 242. The first and second spool members 248, 250 are typically arranged on the support member 252 with an axis of rotation A, B of the first and second spool members 248, 250, respectively, being aligned parallel with each other. In some arrangements, such as the one shown in FIGS. 5A-I, the first and second spool members 248, 250 are arranged radially spaced apart from each other and function independently of each other. In other arrangements, the first and second spool members are arranged coaxially with each other and function independent from each other. In still further arrangements, at least some functionality of the first spool member 248 is dependent on functionality of the second spool member 250, or vise versa.

Figures 5B, 5C:
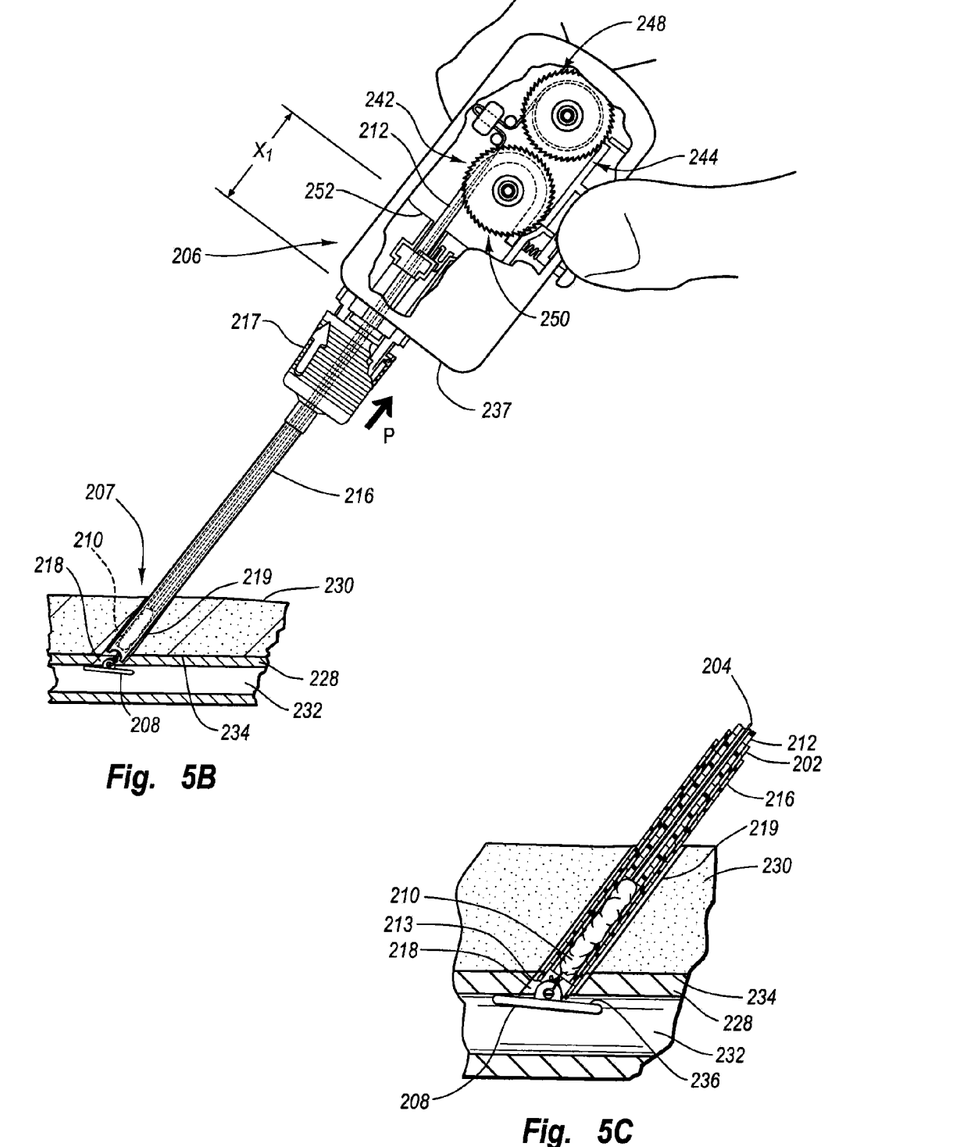
FIG. 5B is a side view of the tissue puncture closure device of FIG. 5A inserted into a procedural sheath and shown engaged with an artery in a first position according to one embodiment of the present disclosure.
FIG. 5C is a detailed inset of FIG. 5B.

In practice, the carrier tube 202 of the closure device 200 is inserted into the procedural sheath 216, which is already inserted within the artery 228 (see FIGS. 5B-5C). As the closure device 200 and the associated closure elements are inserted into the procedural sheath 216, the anchor 208 passes through and out of the distal end of the procedural sheath 216 and is inserted into the artery lumen 232. As mentioned above and shown in FIG. 5A, the anchor 208 is initially arranged substantially flush with the carrier tube 202 to facilitate insertion of the anchor 208 through the percutaneous incision 219 and into the lumen 232.

After the anchor 208 passes out of the distal end of the procedural sheath 216, however, the anchor 208 tends to deploy or rotate to the position shown in FIGS. 5B-5C. The closure device 200 may also be partially withdrawn proximally to catch the anchor 208 on the distal end of the procedural sheath 216 and rotate the anchor 208 to the position shown in FIGS. 5B-5C. The closure device 200 preferably includes a pair of biased finger locking members 215 (see FIG. 5A) that are lockingly received by a matching pair of recesses in the hub 217 of the procedural sheath 216. The locking arrangement between the biased finger locking members 215 and matching recesses preferably restricts relative movement between the closure device 200 and the procedural sheath 216.

Following deployment of the anchor 208, the handle 236 and the procedural sheath 216 are withdrawn together. Withdrawing the handle 236 causes the anchor 208 to anchor itself within the artery 228 against the artery wall 234. With the anchor 208 anchored within the artery 228 at the tissue puncture 218, further retraction of the handle 236 and procedural sheath 216 tends to pull the sealing plug 210 out from the distal end portion 207 of the carrier tube 202, thereby depositing the sealing plug 210 within the incision or percutaneous incision 219. The slit (not shown in the figures) in the carrier tube 202 may permit the distal end portion 207 of the carrier tube to flex or open, facilitating ejection of the sealing plug 210. However, the slit at the distal end portion 207 of the carrier tube 202 may be prevented from opening or flexing by the procedural sheath 216, which is concentric with the carrier tube 202. Therefore, according to principles of the present disclosure, retraction of the handle 236 and procedural sheath 216 causes the procedural sheath 216 to retract with respect to the carrier tube 202 to a second position shown in FIGS. 5D-5E.

Figures 5D, 5E:
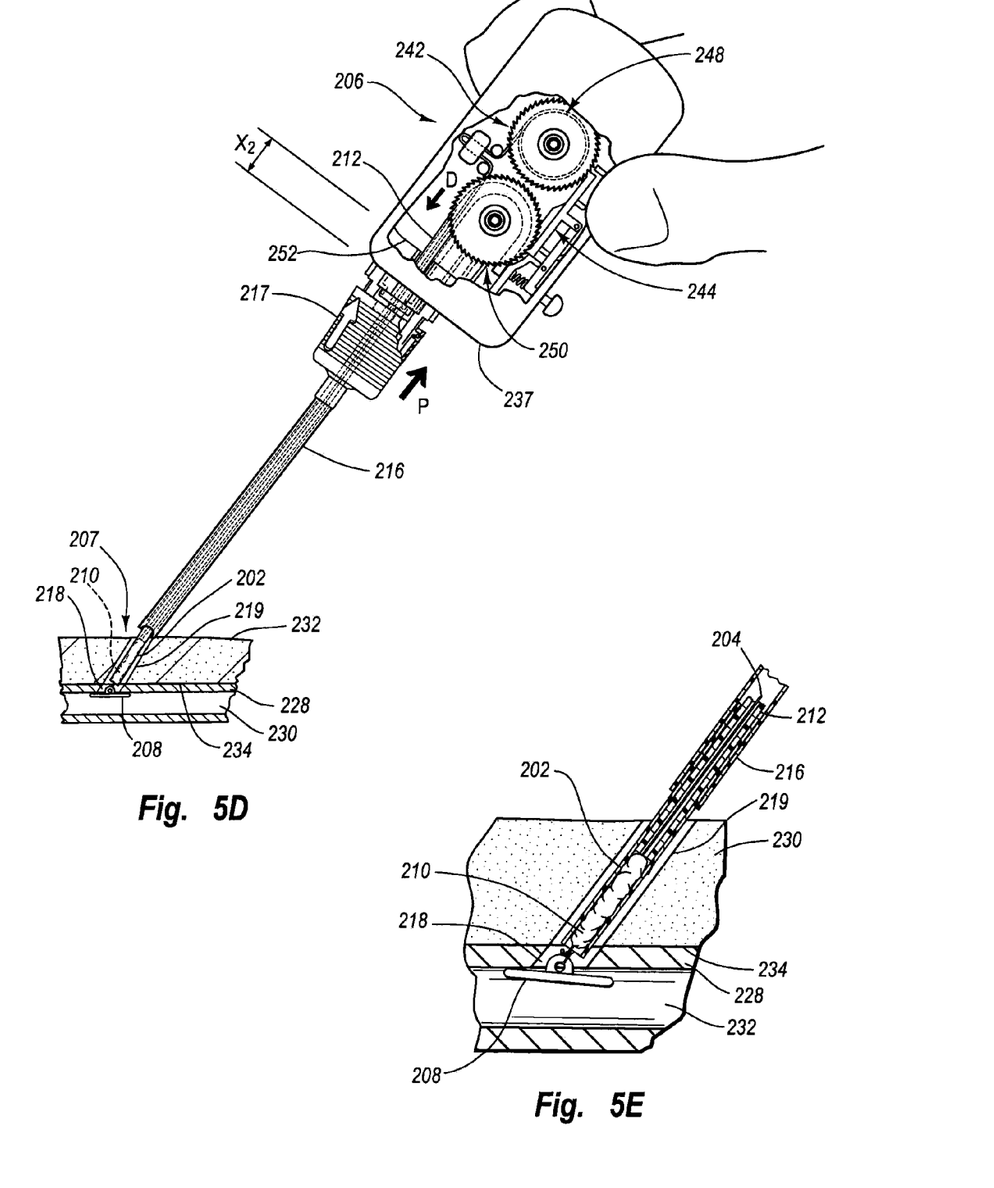
FIG. 5D is a side view of the tissue puncture closure device of FIG. 5A shown engaged with an artery in a second position retracting the procedural sheath.
FIG. 5E is a detailed inset of FIG. 5D.

Referring to FIGS. 5D-5E, the distal end portion 207 of the carrier tube 202 is exposed within the percutaneous incision 219 as the handle 236 and the procedural sheath 216 are retracted proximally in the direction P. The carrier tube 202 retains its position relative to the tissue puncture 218 until the handle 236 and the procedural sheath 216 have been retracted a predetermined distance. Relative movement between the handle 236/procedural sheath 216 and the carrier tube 202 is facilitated by a sliding mount arrangement between the automatic driving assembly 242 and the handle 236. As discussed above, the support member 252, which carries the first and second spool members 248, 250, is movable relative to the handle 236. The carrier tube 202 and automatic driving assembly 242 are mounted, at least in part, to the support member 252.

As shown by a comparison of FIGS. 5A-B with FIG. 5D, the automatic driving assembly 242, which is attached to the carrier tube 202, is displaceable and slides relative to the handle 236 as the handle 236 and procedural sheath 216 are retracted. FIGS. 5A-B show the support member 252, which carries the automatic driving assembly 242, at a distance $X_1$ relative to a front surface 237 of handle 236. FIGS. 5D-E show the the support member 252 shifted distally to a distance $X_2$ relative to the front surface 237. The automatic driving assembly 242 may be initially held in a first position at the distance $X_1$ relative to a front surface 237 of the handle 236 as shown in FIGS. 5A-B. The automatic driving assembly 242 maintains the first position by contact between a stop surface 238 of the handle 236 and a stop member 239 that is mounted to the automatic driving assembly 242. The stop member 239 is configured to release from the stop surface 238 when a predetermined amount of axial force is applied to the handle 236 in the proximal direction P. In one example, the predetermined amount of axial force is in the range of about 0.2 lbs. to about 3.0 lbs., and more preferably in the range of about 0.8 lbs. to about 1.5 lbs. FIG. 5D shows the automatic driving assembly 242 in a second position at the distance $X_2$ relative to the front surface 237 the handle 236.

Retraction of the handle 236 retracts the procedural sheath 216 (which is fixedly connected to the handle 236), but the automatic driving assembly 242 and the carrier tube 202 slide relative to the handle 236 and therefore remain in a fixed position with respect to the tissue puncture 218. The automatic driving assembly 242 may slide a predetermined distance with respect to the handle 236 until the automatic driving assembly 242 reaches a stop surface 238. The predetermined distance is preferably at least long enough to at least partially expose the slit in the carrier tube 202. Further details concerning sliding movement of a driving assembly in a closure device are provided in U.S. Published Patent Application No. 2006/0265006, which is incorporated herein in its entirety by this reference.

When the automatic driving assembly 242 reaches a distal or second position in the handle (see FIG. 5D), further retraction of the handle 236 withdraws the carrier tube 202 as well, thereby ejecting the sealing plug 210 automatically as shown in FIGS. 5D-E. The handle 236 may be further retracted after the automatic driving assembly 242 reaches the second position (i.e., stop surface 238) by release of some suture slack that is available in the first spool member 248. The first spool member rotates in the counter clockwise (CCW) direction to permit release of the suture slack. In one example, the amount of suture slack that is available is about 0.25 inches to about 1.25 inches, and more preferably about 0.7 inches to about 0.9 inches.

Typically, the first spool member 248 is able to rotate in the CCW direction to permit release of the suture slack, but is held from rotating in an opposite, clockwise (CW) direction by a first spool engagement portion 256 of an actuation member 244. The actuation member 244 may also be referred to as an actuation member or an actuator member. In one example, the first spool member 248 may rotate in the first rotation direction under about 0.5 lb. to about 3 lbs. of rotation force or pressure, and more preferably about 1 lbs. to about 2 lbs. of rotation force. When the suture 204 and compaction coiled portion are wrapped around the first and second spool members 248, 250, respectively, in the same direction, the second spool member 250 is typically held from rotating in the CCW direction by a second spool engagement portion 258 of the actuation member 244. The second spool member 250 may be configured to freely rotate in the CW direction under a predetermined amount of rotation force.

Once the suture slack has been released and the sealing plug 210 has been ejected, the handle 236 and carrier tube 202 are restricted from further retraction relative to the patient. At this point, the operator may engage an exposed portion 254 (also referred to as an actuator portion 254) of the actuation member 244. Engaging the actuator portion 254 releases the first and second spool engagement portions 256, 258 from the spool teeth 249, 251 of the first and second spool members 248, 250, respectively.

Upon release from the actuation member 244, the first spool member 248 automatically rotates in the CW direction to further wrap the suture 204 about the first spool member 248, thereby applying a tension force to the suture 204 in a proximal direction P. By placing tension on or pulling the suture 204 away from the percutaneous incision 219, the suture 204 may cinch and lock (with a slip-knot or the like) together the anchor 208 and the sealing plug 210, sandwiching the artery wall 234 between the anchor 208 and sealing plug 210.

Upon release from the actuation member 244, the second spool member 250 automatically rotates in the CCW direction to unwind the coiled portion 246 and advance the compaction tube 212 in the distal direction D. Rotation of the second spool member 250 in the CCW direction provides a torsional motive force that is transduced to a linear compaction force through the coiled portion 246 and the compaction tube 212 to compact the sealing plug 210 toward the anchor 208. The sealing plug 210 is compacted while the handle 236 and carrier tube 202 remain in a fixed position relative to the patient. Compacting the sealing plug 210 may reduce or eliminate any gaps that may otherwise occur between the sealing plug 210 and the tissue puncture 218 in the artery 228.

Figures 5F, 5G:
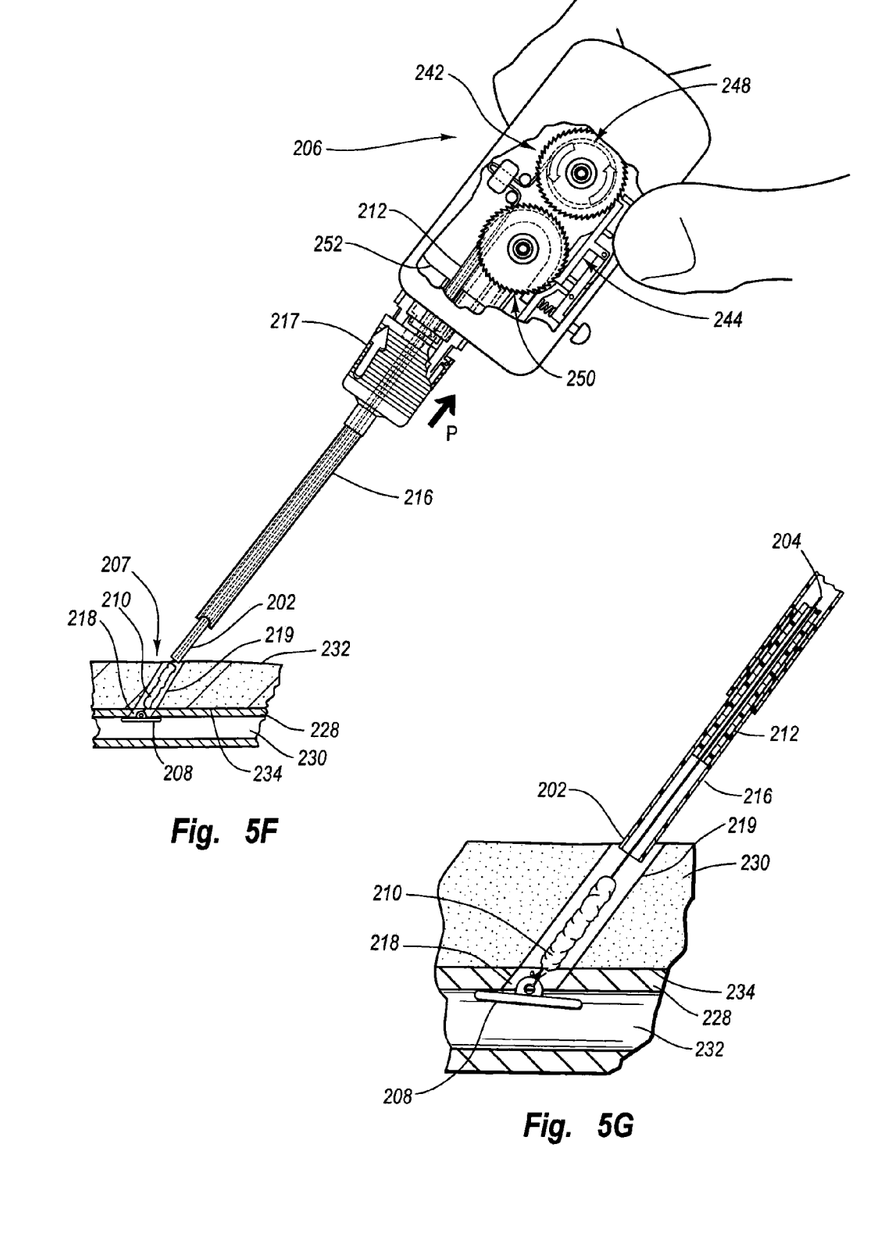
FIG. 5F is a side view of the tissue puncture closure device of FIG. 5A shown engaged with an artery in a third position retracting a carrier tube to expose a sealing plug adjacent to the tissue puncture.
FIG. 5G is a detailed inset of FIG. 5F.
Figures 5H, 5I:
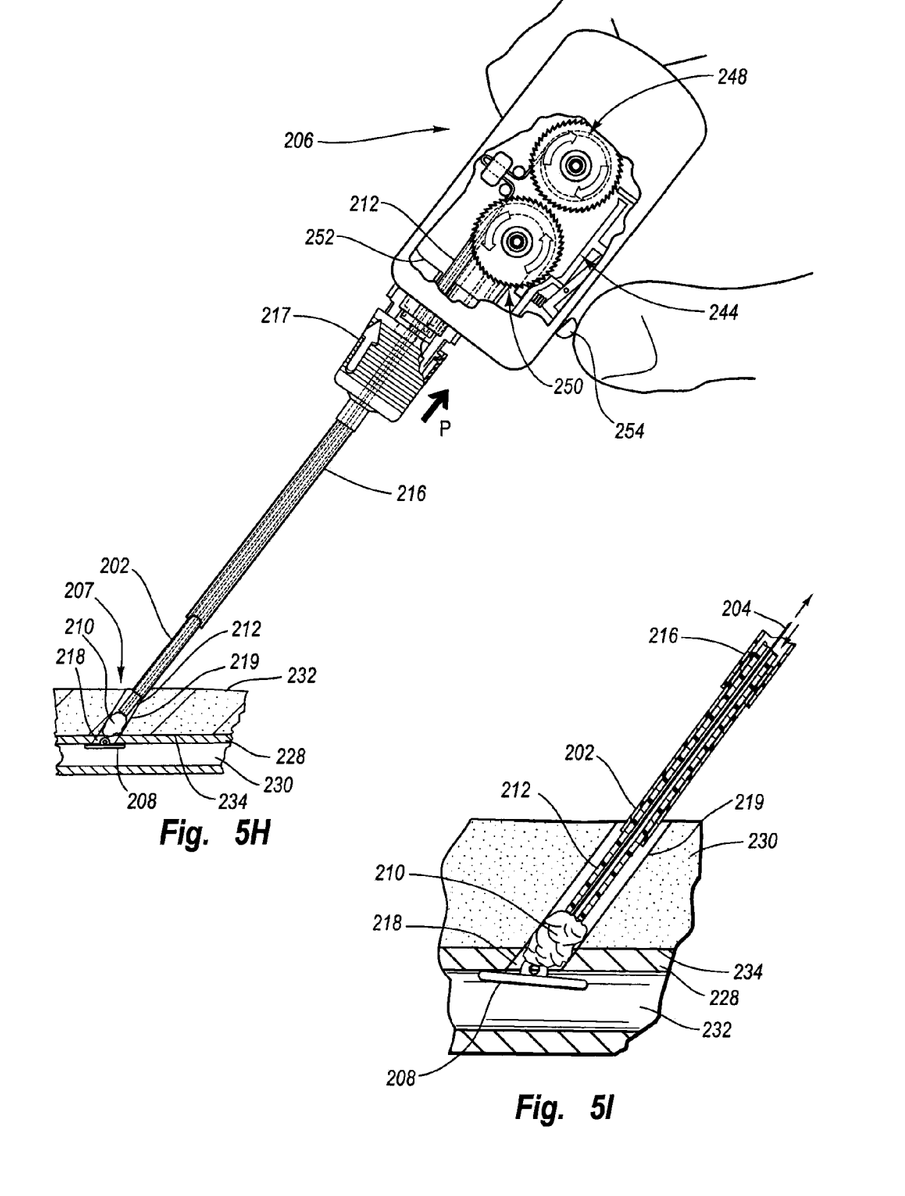
FIG. 5H is a side view of the tissue puncture closure device of FIG. 5A shown engaged with an artery in a fourth position compacting the sealing plug.
FIG. 5I is a detailed inset of FIG. 5H.

The force exerted by the compaction tube 212 and the cinching together of the anchor 208 and sealing plug 210 by the suture 204 also causes the sealing plug 210 to deform radially outward within the percutaneous incision 219. The deformed sealing plug 210 may function as an anchor on the proximal side of the tissue puncture 218 as shown in FIGS. 5H-I.

As the handle 236 of the closure device 200 is retracted from the percutaneous incision 219, the procedural sheath 216 is concurrently retracted (FIGS. 5D-5E). FIGS. 5F-5G show the carrier tube is retracted upon further withdrawl of the handle 236 thereby exposing the sealing plug 210 in the percutaneous incision 219. The sealing plug 210 is compacted automatically upon release of the first and second spool members 248, 250 by contact with the actuator portion 254 (FIGS. 5H-5I).

After the sealing plug 210 has been sufficiently compacted, the automatic driving assembly 242 permits further retraction of the closure device 200 by unwinding of the first spool member 248 in the CCW without additional compaction. With the closure device 200 (i.e., the compaction tube 212 and the carrier tube 202) retracted from the percutaneous incision 219, the suture 204 is exposed for cutting by the operator to separate the sealing plug 210 and anchor 208 from the remainder of the closure device 200.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
    an anchor;
    a sealing plug;
    a suture coupled to the sealing plug;
    a compaction arrangement;
    an automatic driving assembly, comprising:
        a first spool member configured to coil a portion of the suture;
        a second spool member configured to coil a portion of the compaction arrangement;
        an actuation member coupled to the first and second spool members, wherein activation of the actuation member releases the first spool member for rotation thereby applying a tension force in the suture, and wherein activation of the actuation member releases the second spool member for rotation to advance a portion of the compaction arrangement to compress the sealing plug.

2. The tissue puncture closure device of claim 1, further comprising a housing sized to retain the automatic driving assembly, wherein the automatic driving assembly is movable within the housing.

3. The tissue puncture closure device of claim 2, further comprising an insertion sheath connected to the housing.

4. The tissue puncture closure device of claim 1, wherein the compaction arrangement includes a tube portion arranged to compress the sealing plug and a coiled portion at least partially wrapped about the second spool member.

5. The tissue puncture closure device of claim 1, further comprising a housing sized to retain the automatic driving assembly, and the actuation member includes an actuation portion accessible from outside of the housing.

6. The tissue puncture closure device of claim 1, wherein the first and second spool members are operable independent of each other.

7. The tissue puncture closure device of claim 1, wherein the actuation member is configured to concurrently release the first and second spool members.

8. The tissue puncture closure device of claim 1, wherein the actuation member restricts rotation of the first and second spool members in one direction, and the spool members are free to rotate in an opposite direction prior to and after activation of the actuation member.

9. A tissue puncture closure device adapted for partial insertion into and sealing of a tissue puncture in an internal tissue wall accessible through a percutaneous incision, the device comprising:
    an anchor disposed on a distal side of the internal tissue wall;
    a sealing plug disposed on a proximal side of the internal tissue wall;
    a suture coupled at a distal end portion to the anchor and the sealing plug, wherein the sealing plug is slidably disposed on the suture proximal of the anchor;
    a compaction arrangement including a compaction member disposed on the suture and configured to drive the sealing plug along the suture distally towards the anchor;
    a first spool member onto which a proximal end portion of the suture is wound;
    a second spool member onto which a portion of the compaction arrangement is wound;
    an actuation member disengageably coupled to the first and second spool members, wherein activation of the actuation member releases the first spool member to rotate thereby providing a tension force in the suture, and wherein activation of the actuation member releases the second spool member to rotate thereby advancing the compaction member distally to compact the sealing plug.

10. The tissue puncture closure device of claim 9, further comprising a housing, the first and second spool members being slidable within the housing in a distal direction.

11. The tissue puncture closure device of claim 10, further comprising a carrier tube, the sealing plug and the compaction tube being positioned in the carrier tube, the carrier tube being operatively coupled to at least one of the first and second spool members, wherein sliding of the first and second spool members within the housing moves the carrier tube relative to the housing.

12. The tissue puncture closure device of claim 9, wherein the first and second spool members rotate in opposite directions when released by the actuation member.

13. The tissue puncture closure device of claim 9, wherein the first and second spool members are operable independent of each other.

14. The tissue puncture closure device of claim 9, wherein the first and second spool members are arranged non-coaxially relative to each other.

15. A method of sealing a tissue puncture in an internal tissue wall accessible through a percutaneous incision, the method comprising:
- providing a tissue puncture closure device having an anchor, a sealing plug, a suture coupled to the anchor and sealing plug, a compaction arrangement, first and second spool members, and an actuation member, a portion of the suture being wound about the first spool member, and at least a portion of the compaction arrangement being wound about the second spool member;
- inserting the tissue puncture closure device into the percutaneous incision;
- deploying the anchor through the tissue puncture;
- at least partially withdrawing the tissue puncture closure device from the percutaneous incision;
- actuating the actuation member to release the first and second spool members to permit rotation of the first spool member to create tension in the suture and permit rotation of the second spool member to compact the sealing plug toward the anchor with the compaction arrangement.

16. The method of claim 15, wherein the tissue puncture closure device further includes a housing sized to retain at least the first and second spool members, wherein actuating the actuation member includes engaging a portion of the actuation member that is exposed outside of the housing.

17. The method of claim 15, further comprising providing an insertion sheath, inserting the insertion sheath into the percutaneous incision, and inserting a portion of the tissue puncture closure device into the insertion sheath, and deploying the anchor includes advancing the anchor distally beyond a distal end of the insertion sheath.

18. The method of claim 17, further comprising at least partially withdrawing the insertion sheath from the percutaneous incision prior to at least partially withdrawing the closure device.

19. The method of claim 15, wherein the tissue puncture closure device further includes a carrier tube, the sealing plug being positioned in the carrier tube, and at least partially withdrawing the tissue puncture closure device includes at least partially withdrawing the carrier tube and compaction arrangement from the percutaneous incision while leaving the sealing plug positioned in the percutaneous incision.

20. The method of claim 15, wherein at least partially withdrawing the tissue puncture closure device include unwinding a portion of the suture from the first spool member, and actuating the actuation member releases the first spool member to wind up a portion of the suture.

* * * * *